United States Patent [19]
Rumberger et al.

[11] Patent Number: 5,528,138
[45] Date of Patent: Jun. 18, 1996

[54] RESONANT INDUCTIVE DEBRIS DETECTING APPARATUS

[75] Inventors: William E. Rumberger, Newtown Square; Charles R. Gross, Norwood, both of Pa.

[73] Assignee: The Boeing Company, Seattle, Wash.

[21] Appl. No.: 21,272

[22] Filed: Feb. 22, 1993

Related U.S. Application Data

[63] Continuation-in-part of Ser. No. 764,303, Sep. 24, 1991, abandoned.

[51] Int. Cl.$^6$ .......................... G01N 27/74; G01R 33/12; G08B 17/10
[52] U.S. Cl. .......................... 324/204; 324/236; 340/631
[58] Field of Search .......................... 324/204, 234, 324/236, 237, 445, 652, 657, 706, 708; 73/61.42; 340/631

[56] References Cited

U.S. PATENT DOCUMENTS

| | | | |
|---|---|---|---|
| 2,162,009 | 6/1939 | Goldsmith | 175/183 |
| 2,683,030 | 7/1954 | Caule | 265/70 |
| 2,768,684 | 10/1956 | Castel et al. | 164/0.5 |
| 2,772,393 | 11/1956 | Davis | 324/40 |
| 2,902,765 | 9/1959 | Chater | 33/125 |
| 3,142,984 | 8/1964 | Harmon et al. | 73/194 |
| 3,883,796 | 5/1975 | Holt | 324/34 |
| 4,176,545 | 12/1979 | Oddo | 73/64 |
| 4,731,578 | 3/1988 | Tsaprazis | 324/204 |
| 4,831,362 | 5/1989 | Tsarprazis | 340/515 |
| 4,837,511 | 6/1989 | Whittington | 324/236 |
| 5,027,065 | 6/1991 | Bares | 324/204 |
| 5,041,856 | 8/1991 | Veronesi et al. | 324/204 |
| 5,118,410 | 6/1992 | Rumberger | 210/85 |

OTHER PUBLICATIONS

Engine Monitoring System, Bruce D. Nordwall, *Aviation Week & Space Technology*, Mar. 9, 1992.
Electrstatic Engine Monitoring System & Inductive Debris Monitor, Smith Industries–Florham Park Division, Florham Park, NJ.

*Primary Examiner*—Walter E. Snow
*Attorney, Agent, or Firm*—Jones, Tullar & Cooper

[57] ABSTRACT

A debris detecting apparatus is provided which collects debris from a fluid system in a screen member and measures the accumulation of debris by measuring the change of inductance in a coil surrounding a portion of the screen member. A bridge detection means is used which includes the inductive coil as one leg of the bridge. A second sensor in the fluid connected as a second leg of the bridge provides temperature compensation for the bridge. The bridge is excited with a high frequency voltage at or near the resonant frequency of the sensing coil.

12 Claims, 4 Drawing Sheets

RESONANT INDUCTIVE DEBRIS DETECTING APPARATUS

CROSS REFERENCE TO RELATED APPLICATIONS

This application is a continuation in part of application Ser. No. 07/764,303, filed on Sep. 24, 1991, now abandoned and also contains subject matter common to U.S. patent application Ser. No. 07/544,941, filed on Jun. 28, 1990 now U.S. Pat No. 5,118,410 and assigned to the assignee of this invention.

This invention relates in general to an electrical sensing apparatus for sensing the presence of debris in a fluid. More specifically, the present invention relates to an electrical resonant inductive apparatus for indicating the accumulation of debris in a fluid.

BACKGROUND OF THE INVENTION

Fluid systems used in mechanical devices for lubricating purposes or for transmitting power, become contaminated by wear particles from the mechanical components of the device during the life of the machine. Such particles are derived from wear in bearings, gears and other metallic components subject to frictional forces and from components that fracture under excessive stress. The detection of the presence of such debris, and particularly the amount of such debris, has been used to determine the degree of wear occurring in the device and also to predict impending failure by the presence of large amounts of debris. One such apparatus is described in U.S. patent application Ser. No. 07/544,941, filed on Jun. 28, 1990 which is referenced above, and also in U.S. Pat. Nos. 3,878,103 and 3,686,926. This application and these patents describe electro-mechanical devices for detecting the presence of debris in the system and measuring the amount of debris present. These devices all contain a screen for trapping large particles present in the fluid and incorporate with the screen a method of detecting the presence of debris particles. In the issued patents cited, debris is detected when an electrically conductive particle comes in contact with the metallic screen and completes the electrical circuit connected to the wire mesh of the screen. In the U.S. patent application cited above, there is disclosed an apparatus for using the inductive properties of a coil embedded in the screen to measure the amount of debris accumulated. In the two U.S. patents cited, the presence of large amounts of debris is sensed, but progressive, incremental accumulation and the total amount of accumulation cannot be suitably measured. Thus, the sensor often fails to accurately indicate an impending failure of the system and cannot indicate a rate of accumulation which would forecast the impending failure. The U.S. patent application cited will measure debris accumulation and accumulation rate but the sensitivity of the device is limited.

SUMMARY OF THE INVENTION

The present invention overcomes the disadvantages of the prior art by providing a relatively simple device with high sensitivity which produces a high level, useful signal indicating the presence of incremental amounts of debris and the rate of accumulation. This apparatus, like the one disclosed in the patent application cited above, utilizes a screen member for collecting large particles and also contains electrical sensors for detecting the presence of debris in the screen. The primary debris sensors are provided as inductive coil devices having relatively high resonant frequencies whose inductance changes with the presence of debris in the system. The high sensitivity of the device is achieved by tuning the inductive coils at or near their resonant frequency by adding conventional components to the sensor circuit. The sensors are electrically connected as one leg of a conventional bridge circuit. The bridge is excited with a voltage at the resonant frequency of the sensor coils. A second sensor is placed in the fluid stream to provide temperature compensation for the bridge circuit necessary because of the various temperatures involved in the operation of many fluid systems.

DETAILED DESCRIPTION OF THE INVENTION

Figure 1:
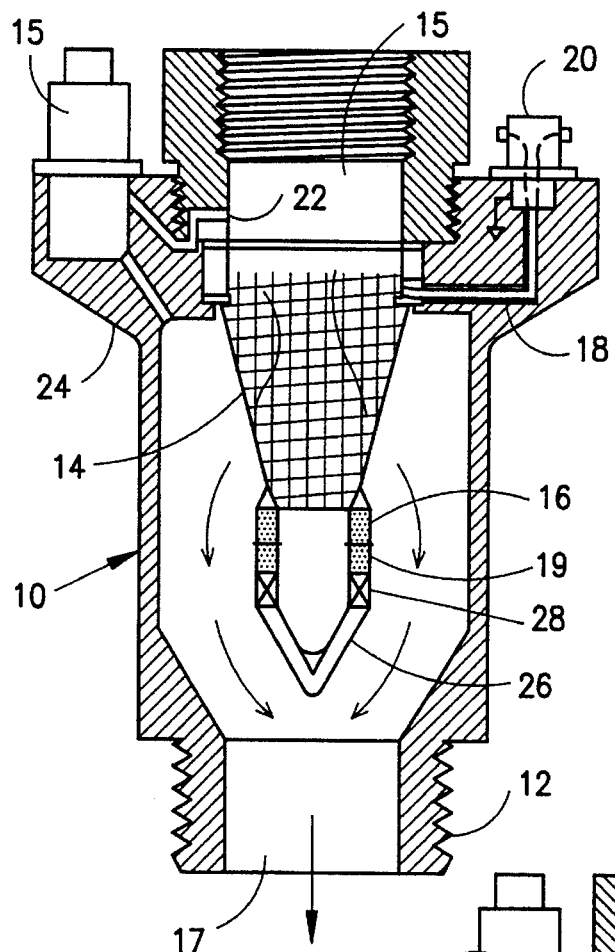
FIG. 1 is a sectional view of a typical device utilizing the invention.

FIG. 1 shows a resonant inductive sensing apparatus 10 according to the present invention. The inductive sensing apparatus 10 comprises a metal housing 12, open at both ends providing an inlet opening 15 and an outlet opening 17 to allow fluid, such as hydraulic, lubricating, or cooling fluid, to flow through in the direction indicated by the arrows. The screen 14 is formed in a conical shape and fluid flowing into the inlet opening 15 escapes through the sides of the screen 14. The lower portion of the screen 14 is formed in a cylindrical shape and sensors 16 and 19 are placed to surround the cylindrical proportion. In this embodiment, the sensor 16 is the primary sensor and the sensor 19 is the compensating sensor providing temperature compensation to the bridge in order to adjust the output of the bridge due to changes in the fluid temperature. The sensors may be of several types which will be described in detail in connection with the discussion of FIGS. 4–7 below. The electrical connections from the sensors 16 and 19 are passed through the housing by means of conduit 18 to a terminal 20 at the top of the housing.

There is also provided a pressure differential sensor 15 which senses the pressure differential between the input and the output of the device by means of conduits 22 and 24. The output of the pressure sensor is an additional output signal which is activated if the housing becomes filled with debris. If the housing fills with debris, the differential pressure between the conduits 22 and 24 will rise rapidly and provide an additional indication of a large amount of debris in the system. The lower portion of the conical screen assembly 26 may be formed as a solid wall or may be formed of screen material. In order to trap additional ferrous material a permanent magnet 28 may be applied below the sensing coil 16.

Figure 2:
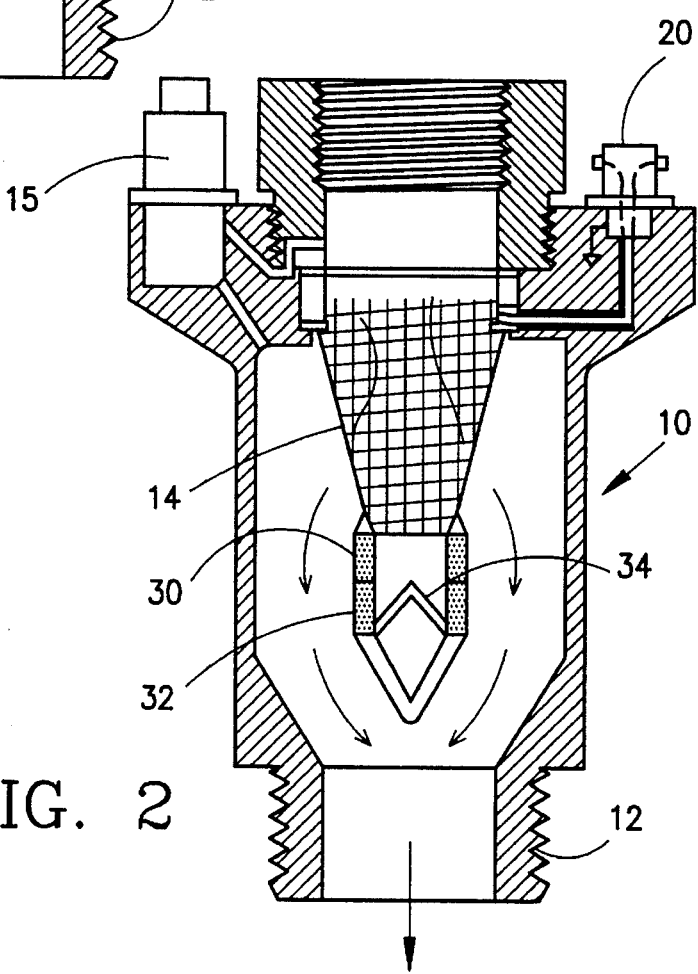
FIG. 2 is a sectional view of an alternate embodiment of the device.

Referring now to FIG. 2, there is shown an alternate embodiment of the invention. In this embodiment, the primary sensing coil 16 and the resistor sensor 19 have been replaced by two tuned inductive coil sensors 30 and 32 assembled one on top of the other about the cylindrical portion of the screen 14. An inverted conical member 34 has been inserted at the bottom of the cylindrical portion of the screen such that its apex is at the junction of the two sensors on the screen. Sensor 32 is the primary sensing coil and sensor 30 is the temperature compensating sensor for the bridge. The conical member 34 causes the accumulated debris to be gathered at the sensing coil 32 thus increasing the sensitivity of the device. If the total particle accumulation reaches the lower edge of coil 30, this sensor will also cause a change in the signal output of the bridge which will alert the user to high debris accumulation.

Figure 3:
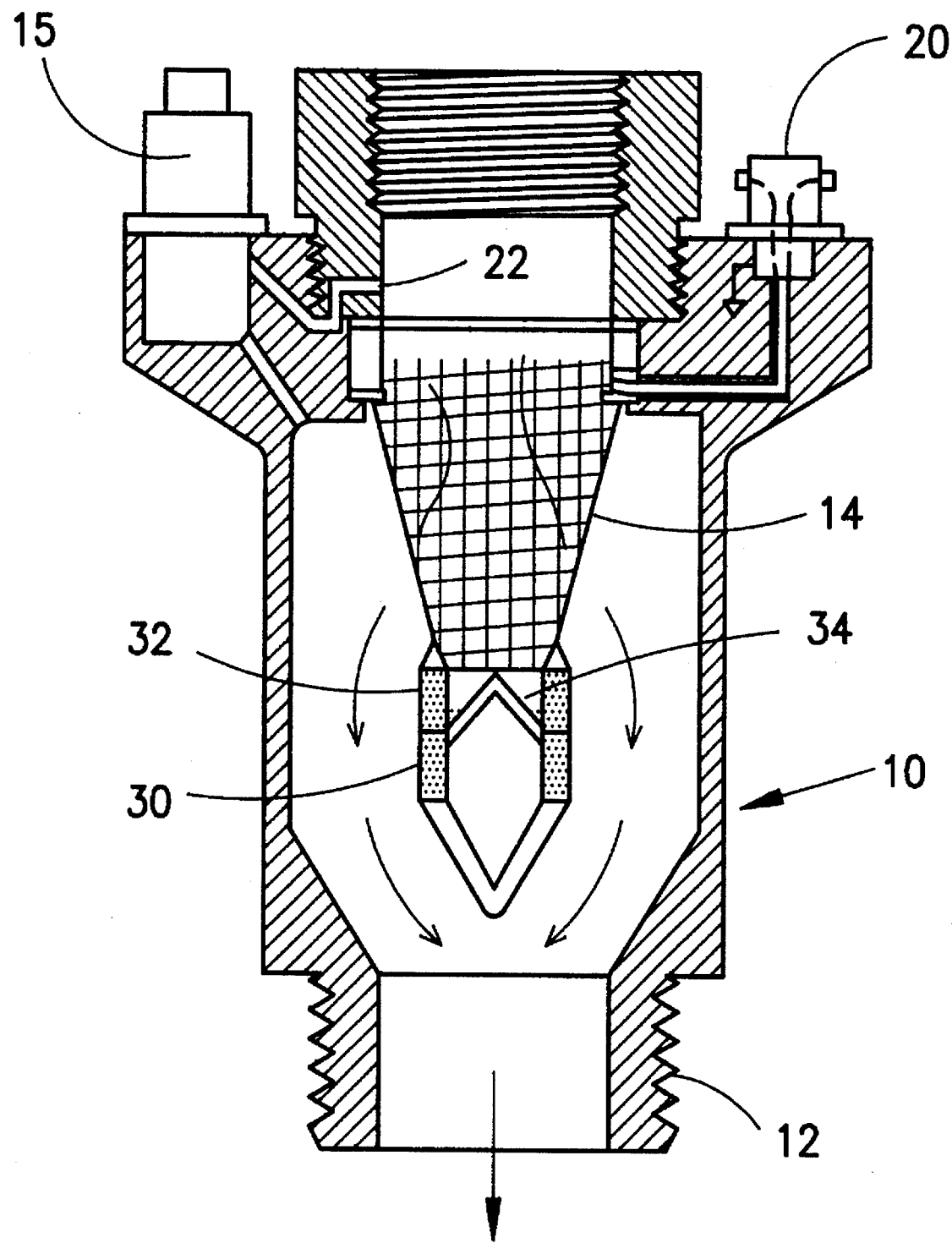
FIG. 3 is a sectional view of yet another alternate embodiment of the system.

Referring now to FIG. 3, there is shown yet another embodiment of the device. In this embodiment the conical member 34 has been placed such that its lower edge is at the junction of the two sensors 30 and 32. The location of the sensors 30 and 32 have been reversed such that the primary sensor 32 is on top and the compensating sensor 30 is on the bottom below the conical member 34. In this configuration all of the debris is collected adjacent the primary sensor 30 and the compensating sensor 32 is unaffected by the accumulated debris.

Figure 4:
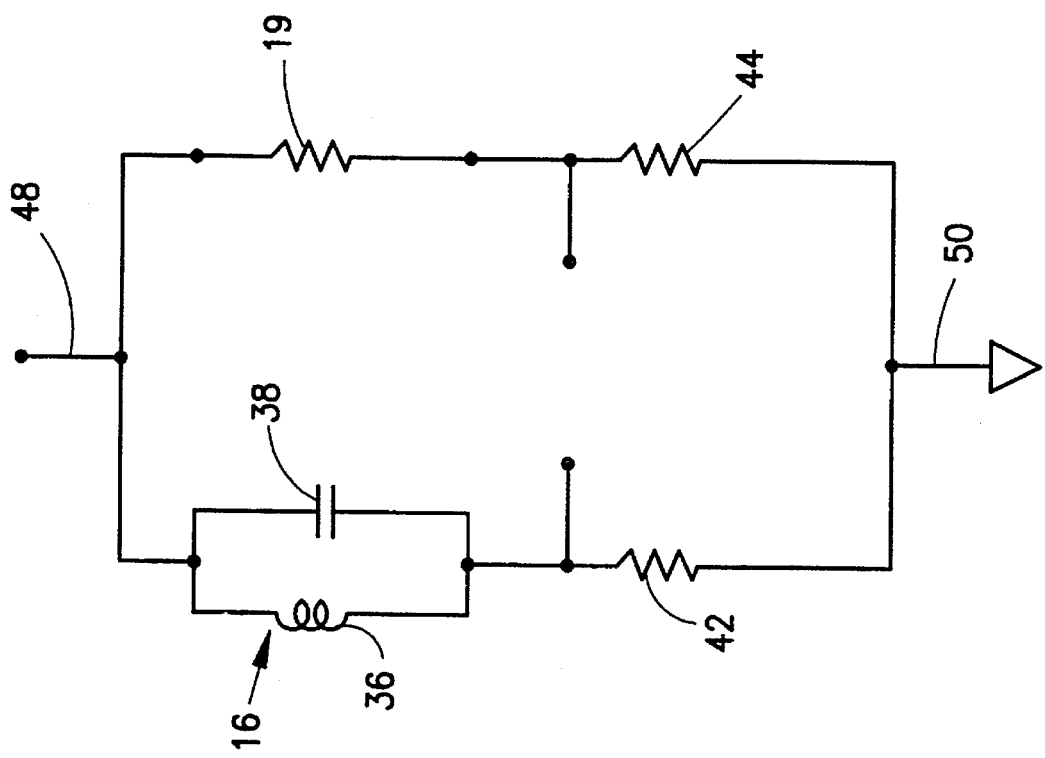
FIG. 4 is a schematic diagram of the a basic embodiment of the device using a coil with a parallel tuning capacitor and a resistor as sensors.

Referring now to FIG. 4, there is shown a schematic of a conventional bridge circuit as used in the embodiment of FIG. 1 comprised of a primary sensor 16 comprising inductive coil 36 and its tuning capacitor 38 connected in parallel with the coil 36 to form one leg of the bridge and a second sensor 19 which is a resistive element installed in the housing to provide temperature compensation for the bridge. To complete the resonant bridge circuit, resistors 44 and 46 are applied to the other two legs of the bridge and may be located outside of the housing of the device. The bridge is excited at input terminal 48 by a high frequency voltage whose frequency is substantially the same as the resonant frequency of the sensor 16. The bridge is connected to ground at terminal 50. The output of the bridge is then measured across terminals 52 and 54 in a conventional manner.

Figure 5:
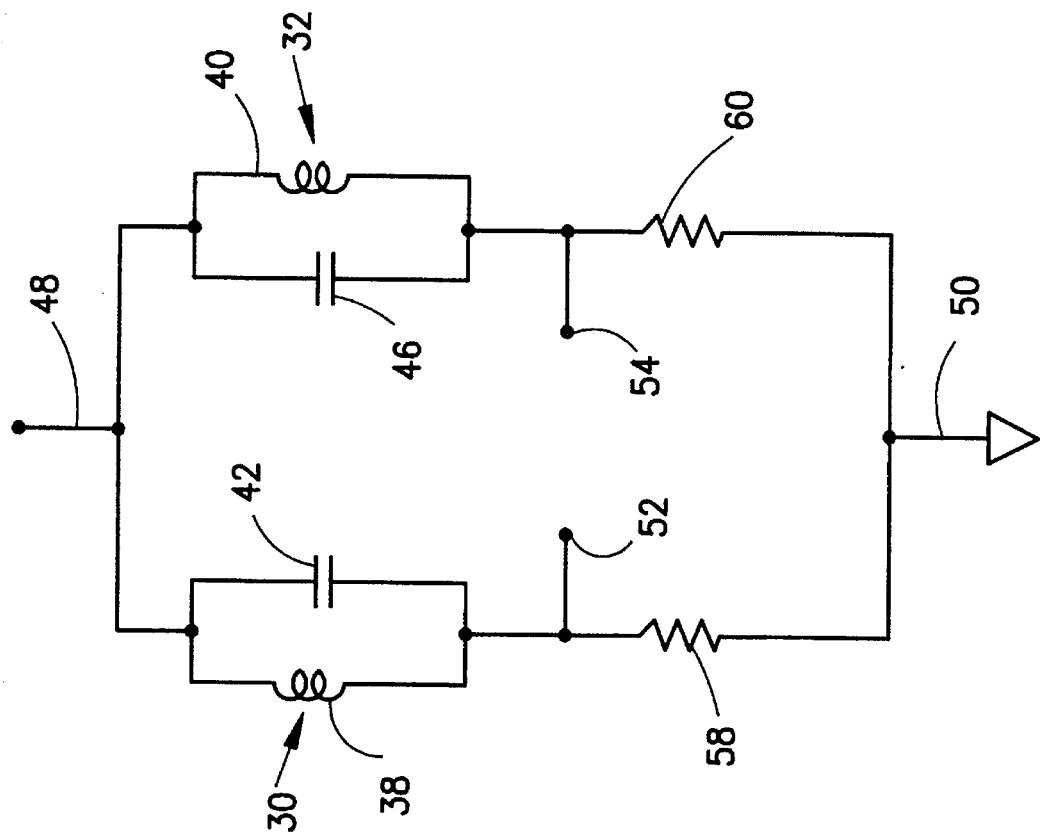
FIG. 5 is an alternate embodiment of the device utilizing two coils tuned with parallel capacitors as sensors in the bridge circuit.

Turning now to FIG. 5, the device may be assembled using a two sensors 30 and 32, each having an inductive coils 38 and 40 respectfully and parallel tuning capacitors 42 and 46 to provide two legs of the bridge circuit. In order to complete the bridge using a dual inductive sensors, resistors 58 and 60 are connected to complete the conventional bridge circuit. As described in connection with the description of the sensor 16 in FIG. 4, the sensors 30 and 32 are tuned by means of the capacitors 40 and 42 to the same resonant frequency and the bridge circuit is excited at that frequency at terminals 48 and 50 in a conventional manner.

Figure 6:
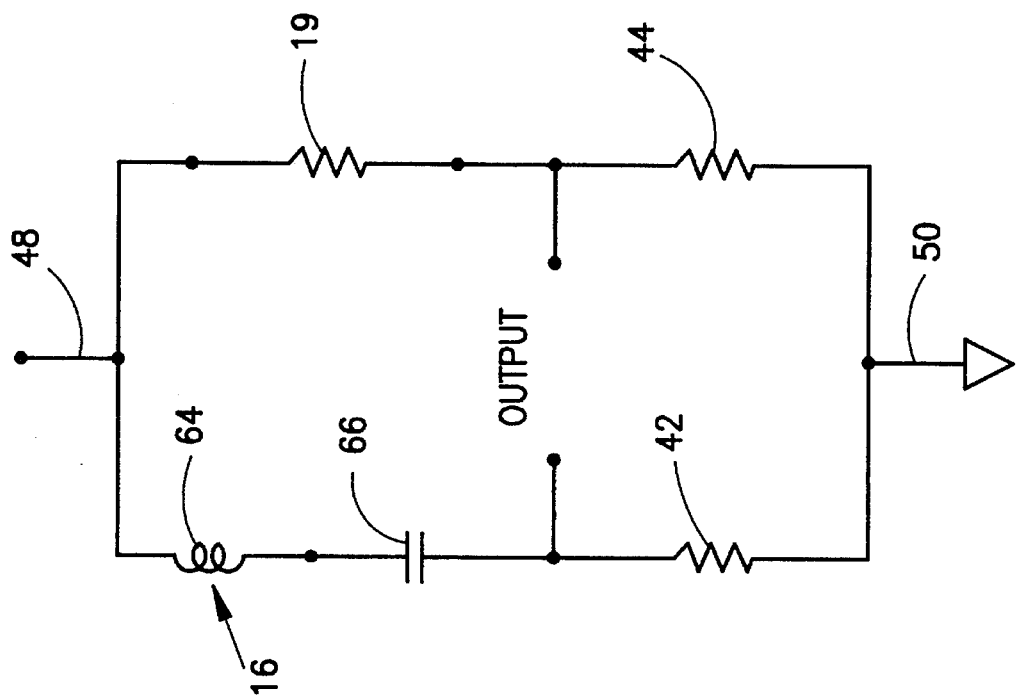
FIG. 6 is a schematic of an alternate embodiment of the device using a series capacitor for tuning the sensor coil and a resistor sensor.

Referring now to FIG. 6, there is shown an embodiment of the invention as an alternate to the embodiment of FIG. 4. In this embodiment, the primary sensor 15' is formed with an inductive coil 44 and a capacitor element 66 connected in series with the coil 64 rather than in parallel as shown in the embodiment of FIG. 4. The remainder of the circuit is substantially the same as that of FIG. 4.

Figure 7:
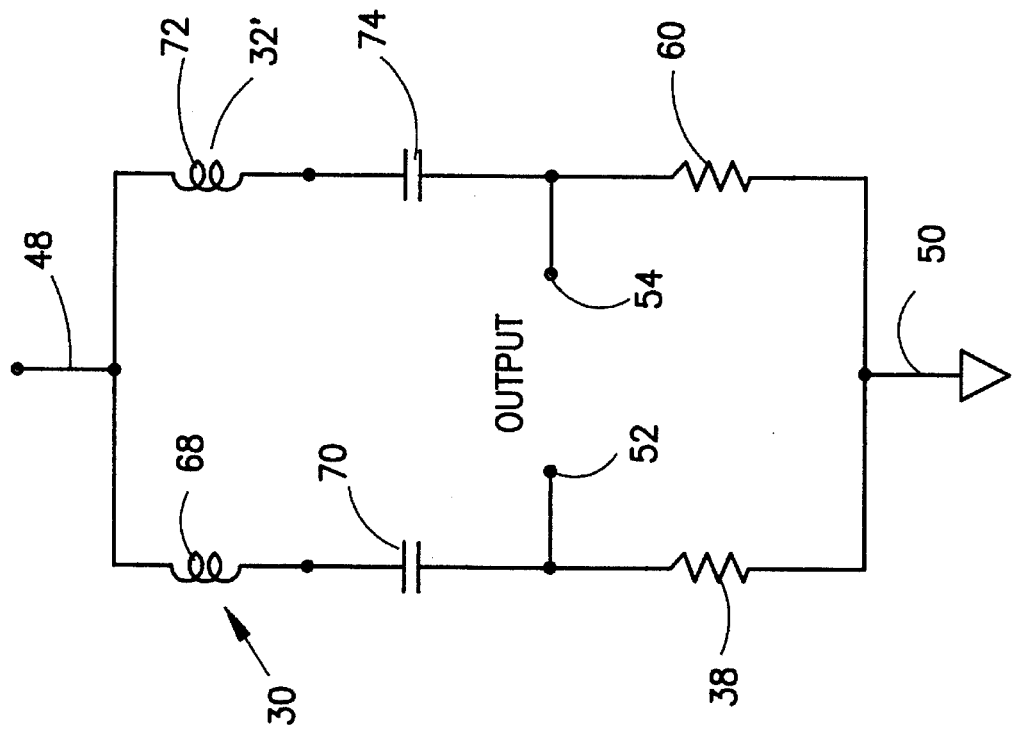
FIG. 7 is an alternate embodiment of the device utilizing two coils tuned with series resistors as sensors in the bridge circuit.

Referring now to FIG. 7, there is shown another embodiment of the invention in which there is provided a primary sensor 30' comprised of an inductive coil 68 and a series tuning capacitor 70 similar to sensor 16' of FIG. 6. The compensating sensor 32' is similar to the primary sensor 30' in that it is also comprised of an inductive coil 72 and a series tuning capacitor 74. The remaining component legs of the bridge are resistors 58 and 60. The bridge is excited at terminal 48 with ground terminal 50 as described in FIGS. 3–6. Again, the sensor coils are tuned to the same resonant frequency and the bridge circuit is excited at that same frequency.

Whether the sensor coil is tuned using a parallel or series resistor will depend upon the application. Each application is different depending on the type, size and amount of debris to be detected. Connecting the components of the measuring means in a bridge circuit is required in order to provide temperature compensation for the device. Since the inductive sensors must operate in the fluid of the monitored system, and since temperature changes alter the inductance of the coil itself, it is necessary to compensate the circuit for the changes in temperature during the operation of the device.

It has been determined by experimental information that exciting the bridge with a frequency voltage at or near the resonant frequency of the inductive coil of the primary sensor increases the sensitivity of the total measuring system. In the preferred embodiment of the invention, the coil of the primary sensor has an inductance of approximately 1.8 millihenrys and the tuning capacitor a value of approximately 120 picofarads which provides the sensor with a resonant frequency between 200 and 300 khz. The bridge is excited with a voltage having a frequency at or near the resonant frequency of the primary sensor with a sinusoidal wave form. Using these values, the disclosed device is capable of detecting 5 milligrams of ferrous wear material introduced inside the coil of the inductor. Materials other than ferrous materials can be sensed by the device. For each material, optimum sensing requires a different frequency for each material. Also, frequency and capacitor values will vary according to the size of the sensing coils. The use of dual resonant inductor coil sensors is desirable for bridge balance and for configuration options. Such options can increase debris capacity as shown in FIG. 2.

Thus, it can be seen that there is provided by this invention a debris measuring device with high sensitivity which can, using conventional electronic means and periodic sampling with time, measure the rate of accumulation of debris as well as the presence of a large amount of debris.

What is claimed is:

1. An apparatus for sensing the presence of and measuring incremental changes in the amount of metallic debris in a fluid system comprising:

a housing having an internal fluid cavity and inlet and outlet openings for conducting fluid through the housing cavity;

a screen member mounted in the fluid cavity between the inlet and outlet openings such that the fluid flows through the screen between the inlet and outlet openings;

a first sensor formed as an inductive coil surrounding a portion of said screen;

a second sensor assembled in the fluid cavity of said housing;

means for tuning said inductive coil of said first sensor to a preselected resonant frequency which is characteristic of the metal of the debris;

a bridge circuit for measuring change in inductance of said first sensor in the presence of debris in said screen member, each of said sensors being connected to said bridge circuit such that each of said sensors forms one leg of said bridge circuit; and electrical supply means for energizing said bridge circuit at approximately the resonant frequency of said first sensor.

2. The apparatus according to claim 1 where said second sensor is a resistor.

3. The apparatus according to claim 1 wherein the means for tuning said inductive coil of said first sensor comprises a capacitor connected in parallel with said inductive coil.

4. The apparatus according to claim 1 wherein the means for tuning said inductive coil of said first sensor comprises a capacitor connected in series with said inductive coil.

5. The apparatus according to claim 1 wherein said second sensor comprises an inductive coil and means for tuning said coil to the same resonant frequency as said first sensor.

6. The apparatus according to claim 5 wherein the means for tuning said inductive coil of said second sensor comprises a capacitor connected in parallel with said inductive coil.

7. The apparatus according to claim 5 wherein the means for tuning said inductive coil of said second sensor comprises a capacitor connected in series with said inductive coil.

8. An apparatus for sensing the presences of and measuring incremental changes in the amount of metallic debris in a fluid system comprising:

a housing having an internal fluid cavity and inlet and outlet openings for conducting fluid through the housing cavity;

a screen member mounted in the fluid cavity between the inlet and outlet openings such that the fluid flows through the screen between the inlet and outlet openings;

a first sensor in the fluid cavity of said housing formed as an inductive coil surrounding a portion of said screen;

a second sensor in the fluid cavity formed as an inductive coil surrounding a portion of said screen below the portion surrounded by said first sensor; means for tuning said inductive coils of both said first and second sensors to the same preselected fixed resonant frequency which frequency is characteristic of the metal of the metallic debris;

a bridge circuit for measuring the change in inductance of said first sensor in the presence of debris in said screen member, each of said sensors being connected to said bridge circuit such that each of said sensors forms one leg of said bridge circuit; and electrical supply means for energizing said bridge circuit at approximately the resonant frequency of said sensors.

9. The apparatus according to claim 8 wherein the means for tuning the inductive coils of said sensors comprises a capacitor connected in parallel with said inductive coils.

10. The apparatus according to claim 8 wherein the means for tuning the inductive coils of said sensors comprises a capacitor connected in series with said inductive coils.

11. The apparatus according to claim 9 and further comprising an inverted conical member inserted inside said screen at the bottom of portions of the screen surrounded by said first and second sensors, the top of said conical member being at the vertical junction of said first and second sensors.

12. The apparatus according to claim 10 and further comprising an inverted conical member inserted inside said screen at the bottom of portions of the screen surrounded by said first and second sensors, the top of said conical member being at the vertical junction of said first and second sensors.

* * * * *